United States Patent
Ganta

(10) Patent No.: US 12,390,516 B2
(45) Date of Patent: Aug. 19, 2025

(54) VACCINES AGAINST TICK-BORNE DISEASES

(71) Applicant: Kansas State University Research Foundation, Manhattan, KS (US)

(72) Inventor: Roman R. Ganta, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 16/631,964

(22) PCT Filed: Jul. 17, 2018

(86) PCT No.: PCT/US2018/042496
§ 371 (c)(1),
(2) Date: Jan. 17, 2020

(87) PCT Pub. No.: WO2019/027670
PCT Pub. Date: Feb. 7, 2019

(65) Prior Publication Data
US 2020/0164055 A1    May 28, 2020

Related U.S. Application Data

(60) Provisional application No. 62/533,550, filed on Jul. 31, 2017.

(51) Int. Cl.
*A61K 39/02* (2006.01)
*A61K 39/00* (2006.01)
*A61P 31/04* (2006.01)

(52) U.S. Cl.
CPC .......... *A61K 39/0233* (2013.01); *A61P 31/04* (2018.01); *A61K 2039/521* (2013.01); *A61K 2039/54* (2013.01); *A61K 2039/542* (2013.01); *A61K 2039/552* (2013.01); *A61K 2039/55566* (2013.01)

(58) Field of Classification Search
None
See application file for complete search history.

(56) References Cited

U.S. PATENT DOCUMENTS

| | | | |
|---|---|---|---|
| 2005/0202046 A1 | 9/2005 | Hu et al. | |
| 2007/0237782 A1 | 10/2007 | Classen | |
| 2010/0239613 A1* | 9/2010 | Harrus | A61K 39/0233 424/234.1 |
| 2012/0045475 A1* | 2/2012 | Browning | A61P 37/04 424/234.1 |

OTHER PUBLICATIONS

Mahan et al. Journal of Veterinary Research, vol. 72, pp. 115-129, 2005. (Year: 2005).*
Stun et al. Acta. Vet. Scand. 57-40 2015. (Year: 2015).*
Thomas et al. PLoS One, vol. 4, issue 11, 2011. (Year: 2011).*
Cong et al. Vaccine vol. 33, pp. 985-992, 2015 (Year: 2015).*
Mahan et al., Vaccine vol. 16 No. 11/12, pp. 1203-1211, 1998 (Year: 1998).*
Ehrlichia_ruminantium_-_Wikipedia.pdf.*

* cited by examiner

*Primary Examiner* — Jana A Hines
*Assistant Examiner* — Khatol S Shahnan Shah
(74) *Attorney, Agent, or Firm* — Sandberg Phoenix & von Gontard, PC; Tracey S. Truitt

(57) ABSTRACT

The present disclosure provides immunogenic compositions and vaccines effective for reducing the incidence of or severity of clinical signs or symptoms of infection by a tick-borne pathogen selected from the group consisting of *Rickettsia rickettsii, Ehrlichia chaffeensis, Ehrlichia canis, Ehrlichia ruminantium, Anaplasma marginale*, and *Anaplasma phagocytophilum*. In preferred forms, the immunogenic composition comprises an inactivated whole cell bacteria selected from the group consisting of *Rickettsia rickettsii, Ehrlichia chaffeensis, Ehrlichia canis, Ehrlichia ruminantium, Anaplasma marginale, Anaplasma phagocytophilum*, and any combination thereof, together with an adjuvant.

5 Claims, No Drawings

VACCINES AGAINST TICK-BORNE DISEASES

BACKGROUND OF THE INVENTION

*Rickettsia rickettsii, Ehrlichia chaffeensis, Ehrlichia canis, Ehrlichia ruminantium, Anaplasma marginale,* and *Anaplasma phagocytophilum* are tick-borne pathogens that cause diseases affecting humans, dogs, horses, and cattle.

Rocky Mountain Spotted Fever (RMSF) is caused by the rickettsial pathogen, *Rickettsia rickettsii. R. rickettsii* is endemic throughout North and Central America. The pathogen is transmitted primarily through the bites of infected ticks. In the USA, *Dermacentor variabilis* (the American dog tick) and *D. andersoni* (the Rocky Mountain wood tick) are the primary vectors for transmitting *R. rickettsii*. Seroprevalence for this pathogen in domestic and stray dogs in disease-endemic regions is estimated to be between 68-81%. Because of the likely high rates of exposure of dogs with ticks, they can serve as sentinels of risk for RMSF in humans. Moreover, clinical and hematological symptoms of RMSF in dogs are very similar to *R. rickettsii* infections in humans. Clinical signs or symptoms following the infection generally include fever, headache, nausea, vomiting, muscle pain, lack of appetite, rash, and can lead to death. The typical treatment for RMSF in dogs and humans is very similar; doxycycline at a dose rate of 5-10 mg/kg/day for 10-21 days or 10-20 mg/kg twice a day for a week. Relapse of RMSF in dogs after doxycycline therapy has also been reported. Sub-clinically infected dogs can also serve as a potential source of infection to ticks and human beings. A vaccine to prevent dog infection can reduce clinical diseases in dogs. The reduced disease in the canine host will also have positive implications in reducing the disease burden in people.

Recovery from a *R. rickettsii* infection confers long lasting protective immunity against subsequent reinfection, suggesting that the availability of a vaccine will be most useful in reducing the RMSF disease in both dogs and people. Currently, no effective vaccine is available to prevent the disease for either people or dogs. There have been attempts to develop a killed vaccine prepared from *R. rickettsii* cultured in ticks or embryonated yolk sac or from cell cultures using non-human primates and guinea pigs as animal models with varying efficacies. These studies, however, are 75-90 years old. Recent studies in mice suggest that the outer membrane protein B (OmpB) and adhesion 2 (Adr2) protein of *R. rickettsii* alone or as in combination serve as protective antigen(s) in reducing the bacterial load. Considering the non-availability of the vaccines for both dogs and people, the goal of the current proposal is to assess both vaccinates, WCV and RAV to generate sufficient preliminary data.

*Ehrlichia chaffeensis* is an obligate intracellular gram-negative species of rickettsiales bacteria. It is a zoonotic pathogen transmitted to humans by the lone star tick (*Amblyomma americanum*). It is the causative agent of human monocytic ehrlichiosis. Patients display early symptoms within 1 to 2 weeks after tick infection. Early symptoms include fever, chills, headache, malaise, low-back pain, conjuctival injection, rash, or gastrointestinal symptoms. Some patients may also have myalgias, arthralgias, and an estimated 10-40% of patients may develop coughing, pharyngitis, diarrhea, vomiting, abdominal pain, and changes in mental status.

*Ehrlichia canis* can cause severe illness in dogs. The disease results from a tick bite and clinical signs are variable in dogs which depend on the differences in the dog breeds, age and the animal immune status. Typically, dogs develop persistent fever, lethargy and depression. Severe weight loss may also occur. Clinically, infected animals may be diagnosed by the swelling of lymph nodes and spleen, and decline in thrombocytes. Dogs may also exhibit signs of anorexia, edema of the limbs or scrotum, and may also exhibit cough. The disease is widespread throughout the world and is associated with the tick infestation. Spontaneous recovery of the animals from clinical signs may occur in some dogs and that the recovered dogs remain asymptomatic although the infection persists for the life of an animal. Clinical signs of chronic ehrlichiosis are variable and may include marked splenomegaly, glomerulonephritis, renal failure, interstitial pneumonitis, anterior uveitis, and meningitis with associated cerebellar ataxia, depression, paresis, and hyperesthesia. Further, chronic infection in a dog will be a source of continued infection acquisition by ticks.

Anaplasmosis is a disease caused by the bacterium *Anaplasma phagocytophilum*. These bacteria are spread to people by tick bites primarily from the blacklegged tick (*Ixodes scapularis*) and the western blacklegged tick (*Ixodes pacificus*). Similar to other vector-borne diseases, symptoms of *Anaplasma phagocytophilum* are often vague and non-specific. Common signs in dogs can include any of the following: loss of appetite, lethargy, lameness, reluctance to move, neck pain or neurologic signs in some cases. In humans, early signs and symptoms (days 1-5) of anaplasmosis are usually mild or moderate and may include fever, chills, severe headache, muscle aches, nausea, vomiting, diarrhea, and loss of appetite. Late signs and symptoms can include respiratory failure, bleeding problems, organ failure, and death.

BRIEF DESCRIPTION OF THE INVENTION

The present disclosure provides an immunogenic composition or vaccine for at least one tick-borne pathogen selected from the group consisting of *R. rickettsii* (which causes Rocky Mountain Spotted Fever (RMSF)), *Ehrlichia chaffeensis* (also referred to as *E. chaffeensis*), *Ehrlichia canis* (also referred to as *E. canis*), *Ehrlichia ruminantium* (also referred to as *E. ruminantium*), *Anaplasma marginale* (also referred to as *A. marginale*), *Anaplasma phagocytophilum* (also referred to as *A. phagocytophilum*), and any combination thereof. This group is also referred to as "tick-borne pathogens of the disclosure". The immunogenic composition or vaccine for a tick-borne pathogen of the disclosure preferably comprises one or more inactivated tick-borne pathogens of the disclosure.

An immunogenic composition or vaccine for RMSF preferably comprises one or more inactivated *R. rickettsii*. In one aspect, the immunogenic composition or vaccine can further comprise one or more additional elements selected from the group consisting of pharmaceutical carriers, stabilizers, adjuvants, compositions known to increase immunity, diluents, and any combination thereof. In a preferred embodiment, the immunogenic composition or vaccine for RMSF comprises one or more *R. rickettsii* and an adjuvant.

The present disclosure further provides for a method of preventing the incidence of or lessening the severity of RMSF in canine or human where the method comprises the step of administering an immunogenic composition or vaccine comprising one or more *R. rickettsii* and an adjuvant to an animal in need thereof, preferably a canine or human.

The present disclosure additionally provides for a method of reducing clinical symptoms of RMSF or reducing the incidence or severity of clinical symptoms of RMSF, where the step of the method includes administration of an immunogenic composition or vaccine comprising one or more *R. rickettsii* and an adjuvant to an animal in need thereof, preferably a canine or human.

A method for preventing subclinical infection of *R. rickettsii* in a canine is also provided in the present disclosure. The method for preventing subclinical infection of *R. rickettsii* includes the step of administration of an immunogenic composition or vaccine comprising one or more inactivated *R. rickettsii* and an adjuvant to an animal in need thereof, preferably a canine or human.

An immunogenic composition or vaccine for *Ehrlichia chaffeensis* or *Ehrlichia ruminantium* preferably comprises one or more inactivated *E. chaffeensis* or *Ehrlichia ruminantium*. In one aspect, the immunogenic composition or vaccine can further comprise one or more additional elements selected from the group consisting of pharmaceutical carriers, stabilizers, adjuvants, compositions known to increase immunity, diluents, and any combination thereof. In a preferred embodiment, the immunogenic composition or vaccine for *Ehrlichia chaffeensis* or *Ehrlichia ruminantium* comprises one or more *E. chaffeensis* or *Ehrlichia ruminantium* and an adjuvant.

The present disclosure further provides for a method of preventing the incidence of or lessening the severity of infection from *Ehrlichia chaffeensis* or *Ehrlichia ruminantium* in canine or human where the method comprises the step of administering an immunogenic composition or vaccine comprising one or more *E. chaffeensis* or *Ehrlichia ruminantium* and an adjuvant to an animal in need thereof, preferably a canine or human.

The present disclosure additionally provides for a method of reducing clinical symptoms of infection from *Ehrlichia chaffeensis* or *Ehrlichia ruminantium* or reducing the incidence or severity of clinical symptoms of such infection, where the step of the method includes administration of an immunogenic composition or vaccine comprising one or more *E. chaffeensis* or *Ehrlichia ruminantium* and an adjuvant to an animal in need thereof, preferably a canine or human.

A method for preventing subclinical infection of *E. chaffeensis* or *Ehrlichia ruminantium* in a canine or human is also provided in the present disclosure. The method for preventing subclinical infection of *E. chaffeensis* or *Ehrlichia ruminantium* includes the step of administration of an immunogenic composition or vaccine comprising one or more inactivated *E. chaffeensis* or *Ehrlichia ruminantium* and an adjuvant to an animal in need thereof, preferably a canine or human.

An immunogenic composition or vaccine for *Ehrlichia canis* preferably comprises one or more inactivated *E. canis*. In one aspect, the immunogenic composition or vaccine can further comprise one or more additional elements selected from the group consisting of pharmaceutical carriers, stabilizers, adjuvants, compositions known to increase immunity, diluents, and any combination thereof. In a preferred embodiment, the immunogenic composition or vaccine for *Ehrlichia canis* comprises one or more *E. canis* and an adjuvant.

The present disclosure further provides for a method of preventing the incidence of or lessening the severity of infection from *Ehrlichia canis* in canine where the method comprises the step of administering an immunogenic composition or vaccine comprising one or more *E. canis* and an adjuvant to an animal in need thereof, preferably a canine.

The present disclosure additionally provides for a method of reducing clinical symptoms of infection from *Ehrlichia canis* or reducing the incidence or severity of clinical symptoms of such infection, where the step of the method includes administration of an immunogenic composition or vaccine comprising one or more *E. canis* and an adjuvant to an animal in need thereof, preferably a canine.

A method for preventing subclinical infection of *E. canis* in a canine is also provided in the present disclosure. The method for preventing subclinical infection of *E. canis* includes the step of administration of an immunogenic composition or vaccine comprising one or more inactivated *E. canis* and an adjuvant to an animal in need thereof, preferably a canine.

An immunogenic composition or vaccine for *Anaplasma phagocytophilum* or *Anaplasma marginale* preferably comprises one or more inactivated *Anaplasma phagocytophilum* or *Anaplasma marginale*. In one aspect, the immunogenic composition or vaccine can further comprise one or more additional elements selected from the group consisting of pharmaceutical carriers, stabilizers, adjuvants, compositions known to increase immunity, diluents, and any combination thereof. In a preferred embodiment, the immunogenic composition or vaccine for *Anaplasma phagocytophilum* or *Anaplasma marginale* comprises one or more *Anaplasma phagocytophilum* or *Anaplasma marginale* and an adjuvant.

The present disclosure further provides for a method of preventing the incidence of or lessening the severity of infection from *Anaplasma phagocytophilum* or *Anaplasma marginale* in canine or human where the method comprises the step of administering an immunogenic composition or vaccine comprising one or more *Anaplasma phagocytophilum* or *Anaplasma marginale* and an adjuvant to an animal in need thereof, preferably a canine or human.

The present disclosure additionally provides for a method of reducing clinical symptoms of infection from *Anaplasma phagocytophilum* or *Anaplasma marginale* or reducing the incidence or severity of clinical symptoms of such infection, where the step of the method includes administration of an immunogenic composition or vaccine comprising one or more *Anaplasma phagocytophilum* or *Anaplasma marginale* and an adjuvant to an animal in need thereof, preferably a canine or human.

A method for preventing subclinical infection of *Anaplasma phagocytophilum* or *Anaplasma marginale* in a canine or human is also provided in the present disclosure. The method for preventing subclinical infection of *Anaplasma phagocytophilum* or *Anaplasma marginale* includes the step of administration of an immunogenic composition or vaccine comprising one or more inactivated *Anaplasma phagocytophilum* or *Anaplasma marginale* and an adjuvant to an animal in need thereof, preferably a canine or human.

DETAILED DESCRIPTION OF THE INVENTION

The present disclosure provides an immunogenic composition or vaccine for *Rickettsia rickettsii, Ehrlichia chaffeensis, Ehrlichia canis, Ehrlichia ruminantium, Anaplasma marginale*, and/or *Anaplasma phagocytophilum*, where the immunogenic composition or vaccine comprises one or more inactivated *R. rickettsii, E. chaffeensis, E. ruminantium, E. canis, A. marginale A. phagocytophilum*, and any combination thereof. In preferred forms, the immunogenic composition or vaccine further includes or comprises an adjuvant.

The present disclosure further provides for a method of preventing or lessening the severity of *R. rickettsii, E. chaffeensis, E. ruminantium, A. marginale*, and/or *A. phagocytophilum* in canine or human and of *E. canis* in a dog where the method comprises the step of administering an immunogenic composition or vaccine comprising one or more *R. rickettsii E. chaffeensis, E. canis, E. ruminantium, A. marginale*, and/or *A. phagocytophilum* and an adjuvant to a canine or human.

The present disclosure additionally provides for a method of reducing clinical symptoms of infection from *R. rickettsii, E. chaffeensis*, and/or *A. phagocytophilum* in canine or human and of *E. canis, E. ruminantium*, and/or *A. marginale* in a dog or reducing the incidence or severity of clinical symptoms of infection from *R. rickettsii, E. chaffeensis*, and/or *A. phagocytophilum* in canine or human and of *E. canis, E. ruminantium*, and/or *A. marginale* in a dog, where the step of the method includes administration of an immunogenic composition or vaccine comprising one or more *R. rickettsii, E. chaffeensis*, and/or *A. phagocytophilum* in canine or human and of *E. canis, E. ruminantium*, and/or *A. marginale* in a dog and an adjuvant to a canine or human.

The clinical symptoms of RMSF caused by *R. rickettsia* reduced or reduced in incidence or severity include, but are not limited to, loss of appetite, fever, pain in muscles and joints, depression, swollen lymph nodes, edema, coughing, difficulty breathing, vomiting, blood in the stool, dizziness, ataxia, seizures, nose bleeds, retina bleeding, blood in the urine, pinpoint bruises that appear on the lining of the eyelids and mouth, irregular heartbeat, difficulty with clotting leading to shock or death, and any combination thereof. Preferably the clinical symptoms associated with RMSF are reduced in frequency and/or severity by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or reduced by 100% in comparison to an animal or group of animals that has been subjected to the same challenge conditions but did not receive an administration of the immunogenic composition or vaccine.

The clinical symptoms caused by *E. chaffeensis* reduced or reduced in incidence or severity include, but are not limited to, fever, chills, headache, malaise, low-back pain, conjuctival injection, rash, gastrointestinal symptoms, myalgias, arthralgias, coughing, pharyngitis, diarrhea, vomiting, abdominal pain, changes in mental status, and any combination thereof. Preferably the clinical symptoms associated with *E. chaffeensis* are reduced in frequency and/or severity by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or reduced by 100% in comparison to an animal or group of animals that has been subjected to the same challenge conditions but did not receive an administration of the immunogenic composition or vaccine.

The clinical symptoms caused by *E. canis* or *E. ruminantium* reduced or reduced in incidence or severity include, but are not limited to, fever, lethargy, depression swelling of lymph nodes, swelling of the spleen, decline in thrombocytes, anorexia, edema of the limbs or scrotum, cough, glomerulonephritis, renal failure, interstitial pneumonitis, anterior uveitis, meningitis with associated cerebellar ataxia, paresis, hyperesthesia, and any combination thereof. Preferably the clinical symptoms associated with *E. canis* are reduced in frequency and/or severity by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or reduced by 100% in comparison to an animal or group of animals that has been subjected to the same challenge conditions but did not receive an administration of the immunogenic composition or vaccine.

The clinical symptoms caused by *A. marginale* or *A. phagocytophilum* reduced or reduced in incidence or severity include, but are not limited to, loss of appetite, lethargy, lameness, reluctance to move, neck pain, neurologic signs, fever, chills, severe headache, muscle aches, nausea, vomiting, diarrhea, loss of appetite, respiratory failure, bleeding problems, organ failure, death, and any combination thereof. Preferably the clinical symptoms associated with *E. canis* are reduced in frequency and/or severity by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or reduced by 100% in comparison to an animal or group of animals that has been subjected to the same challenge conditions but did not receive an administration of the immunogenic composition or vaccine.

The present disclosure also provides a method for preventing subclinical infection of at least one of *R. rickettsii, E. chaffeensis*, and/or *A. phagocytophilum* in a canine or human and of *E. canis, E. ruminantium*, and/or *A. marginale* in a canine is also provided in the present disclosure. The method for preventing subclinical infection of at least one of *R. rickettsii, E. chaffeensis, A. phagocytophilum*, and/or *E. canis, E. ruminantium*, and/or *A. marginale* includes the step of administration of an immunogenic composition or vaccine comprising one or more inactivated *R. rickettsii, E. chaffeensis, A. phagocytophilum* and an adjuvant to a canine or human or one or more inactivated *E. canis, E. ruminantium*, and/or *A. marginale* to a canine.

In other aspect, the present disclosure provides a method for reducing the bacterial load of at least one tick-borne pathogen of the disclosure in a canine or human, where the method comprises the step of administration of an immunogenic composition or vaccine comprising one or more inactivated tick-borne pathogens selected from the group consisting of *Rickettsia rickettsii, Ehrlichia chaffeensis, Ehrlichia canis, Ehrlichia ruminantium, Anaplasma marginale, Anaplasma phagocytophilum*, or any combination thereof and an adjuvant to a canine or human. Preferably, the bacterial load is reduced at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% and 100% in comparison to an animal or group of animals that has been subjected to the same challenge conditions but did not receive an administration of the immunogenic composition or vaccine.

The one or more inactivated tick-borne pathogen of the present disclosure may be inactivated using any method known to prevent the bacteria from replicating in a host. Inactivation may be accomplished by a method selected from, but not limited to, heat inactivated, formalin inactivated, or any method used to provide a killed bacteria.

The one or more inactivated tick-borne pathogen of the present disclosure may be any whole cell *Rickettsia rickettsii, Ehrlichia chaffeensis, Ehrlichia canis, Ehrlichia ruminantium, Anaplasma marginale*, and *Anaplasma phagocytophilum* capable of producing their respective pathogen or associated disease or signs or symptoms of infection in their active form. Preferred strains of *R. rickettsia*, include, but are not limited to Shelia Smith strain, Strain R, Iowa strain, Sao Paulo strain, Morgan strain, Hino strain, Hauke strain, Arizona strain, Brazil strain, HLP2 strain, and any combination thereof.

In a preferred aspect, the one or more *R. rickettsii* have at least 75%, at least 80%, at least 85%, at least 90%, at least 95%, at least 96%, at least 97%, at least 98%, and at least 99% sequence identity or homology with a strain of *R. rickettsii* selected from the Shelia Smith strain, Strain R, Iowa strain, Sao Paulo strain, Morgan strain, Hino strain, Hauke strain, Arizona strain, Brazil strain, and the HLP2 strain of *R. rickettsii*. Further, in an embodiment where more than one strain of *R. rickettsii* is present, the immunogenic composition or vaccine of the present disclosure may include more than one strain within a single composition.

Preferred strains of *E. canis*, include, but are not limited to PDE, VDE, VTE, VHE, Oklahoma, Florida, 611, Gzh982, Germishuys, Gxht67, Gdt3, 95E10, Oviina, Kagoshima, Madrid, Greece1, Greece0, Thai, and Okinawa.

In a preferred aspect, the one or more *E. canis* have at least 75%, at least 80%, at least 85%, at least 90%, at least 95%, at least 96%, at least 97%, at least 98%, and at least 99% sequence identity or homology with a strain of *E. canis* selected from the group consisting of PDE, VDE, VTE, VHE, Oklahoma, Florida, 611, Gzh982, Germishuys, Gxht67, Gdt3, 95E10, Oviina, Kagoshima, Madrid, Greece1, Greece0, Thai, and Okinawa. Further, in an embodiment where more than one strain of *E. canis* is present, the immunogenic composition or vaccine of the present disclosure may include more than one strain within a single composition.

Preferred strains of *E. chaffeensis*, include, but are not limited to Arkansas, Liberty, Wakulla, Jax, St. Vincent, Sapulpa, Osceola, 91HE17, and West Paces.

In a preferred aspect, the one or more *E. chaffeensis* have at least 75%, at least 80%, at least 85%, at least 90%, at least 95%, at least 96%, at least 97%, at least 98%, and at least 99% sequence identity or homology with a strain of *E. chaffeensis* selected from the group consisting of Arkansas, Liberty, Wakulla, Jax, St. Vincent, Sapulpa, Osceola, 91HE17, and West Paces. Further, in an embodiment where more than one strain of *E. chaffeensis* is present, the immunogenic composition or vaccine of the present disclosure may include more than one strain within a single composition.

Preferred strains of *A. phagocytophilum*, include, but are not limited to Ap-Variant1, Ap-ha, NCH-1, Sardinian, HZ, ApMuc01c and ApMuc02c.

In a preferred aspect, the one or more *A. phagocytophilum* have at least 75%, at least 80%, at least 85%, at least 90%, at least 95%, at least 96%, at least 97%, at least 98%, and at least 99% sequence identity or homology with a strain of *A. phagocytophilum* selected from the group consisting of Ap-Variant1, Ap-ha, NCH-1, Sardinian, HZ, ApMuc01c and ApMuc02c. Further, in an embodiment where more than one strain of *A. phagocytophilum* is present, the immunogenic composition or vaccine of the present disclosure may include more than one strain within a single composition.

The immunogenic composition or vaccine of the present disclosure preferably includes an adjuvant. The adjuvant for purposes of the present disclosure may be selected from any adjuvant suitable for use in canines. Preferred adjuvants include, but are not limited to Freund's incomplete adjuvant and Montanide.

The immunogenic composition or vaccine of the present invention may be administered in any dose necessary to provide an immune response in or to a canine or human. Their administration modes, dosages and optimum pharmaceutical forms can be determined according to the criteria generally taken into account in the establishment of a treatment adapted to an animal such as, for example, the age or the weight, the seriousness of its general condition, the tolerance to the treatment and the secondary effects noted. Preferably, the vaccine of the present disclosure is administered in an amount that is protective against RMSF or infection by *Rickettsia rickettsii, Ehrlichia chaffeensis, Ehrlichia canis, Ehrlichia ruminantium, Anaplasma marginale*, and *Anaplasma phagocytophilum*, or any combination thereof.

According to a further embodiment, the immunogenic composition or vaccine is administered to canines or humans in one or two doses at an interval of about 2 to 4 weeks. For example, the first administration is performed when the animal or human is about 2 to 3 weeks to about 8 weeks of age. The second administration is performed about 1 to about 4 weeks after the first administration of the first vaccination. According to a further embodiment, revaccination is performed in an interval of 3 to 12 month after administration of the second dose. Administration of subsequent vaccine doses is preferably done on a 6 month to an annual basis. In another preferred embodiment, animals vaccinated before the age of about 2 to 3 weeks should be revaccinated. Administration of subsequent vaccine doses is preferably done on an annual basis. In an alternate embodiment, the immunogenic composition or vaccine of the present disclosure is effective after a single dose administration, therefore, in such an embodiment, the immunogenic composition or vaccine would only need to be administered a single time.

In a further embodiment, the immunogenic composition of the present disclosure is administered in an amount of from about $10^2$ to about $10^9$ $TCID_{50}$ per dose, preferably about $10^3$ to about $10^8$ $TCID_{50}$ per dose, more preferably, about $10^4$ to about $10^8$ $TCID_{50}$ per dose, where values such as $10^2$ $TCID_{50}$ per dose, $10^3$ $TCID_{50}$ per dose, $10^4$ $TCID_{50}$ per dose, $10^5$ $TCID_{50}$ per dose, $10^6$ $TCID_{50}$ per dose, $10^7$ $TCID_{50}$ per dose, $10^8$ $TCID_{50}$ per dose, and $10^9$ $TCID_{50}$ per dose are envisioned.

In another embodiment, the immunogenic composition of the present disclosure includes at least $10^3$ bacteria per administration or per dose, more preferably, $10^3$-$10^{11}$ bacteria per dose, still more preferably $10^4$-$10^{10}$ bacteria per dose, even more preferably $10^5$-$10^8$ bacteria per dose, and still more preferably $10^6$-$10^7$ bacteria per dose.

These compounds can be administered by the systemic route, in particular by the intravenous route, by the intramuscular, intradermal or subcutaneous route, or by the oral route. In a more preferred manner, the immunogenic composition or vaccine according to the disclosure will be administered by the intravenous route.

Their administration modes, dosages and optimum pharmaceutical forms can be determined according to the criteria generally taken into account in the establishment of a treatment adapted to an animal such as, for example, the age or the weight, the seriousness of its general condition, the tolerance to the treatment and the secondary effects noted. Preferably, the vaccine of the present disclosure is administered in an amount that is protective against RMSF or against signs or symptoms of infection from *Rickettsia rickettsii, Ehrlichia chaffeensis, Ehrlichia canis, Ehrlichia*

*ruminantium, Anaplasma marginale, Anaplasma phagocytophilum*, or any combination thereof.

An "immunogenic composition" refers to a composition of matter that comprises at least one antigen which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction in the severity or prevalence of, up to and including a lack of symptoms normally displayed by an infected host, a quicker recovery time and/or a lowered viral titer in the infected host.

"Incidence" in clinical signs or symptoms can refer to either the overall number of clinical signs or symptoms present in an individual animal or can refer to the relative number of animals in a group of animals that exhibit clinical signs or symptoms.

"Adjuvants" as used herein, can include montanide, Freund's incomplete adjuvant, aluminum hydroxide and aluminum phosphate, saponins e.g., Quil A, QS-21 (Cambridge Biotech Inc., Cambridge MA), GPI-0100 (Galenica Pharmaceuticals, Inc., Birmingham, AL), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Among the copolymers of maleic anhydride and alkenyl derivative, the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta GA), SAF-M (Chiron, Emeryville California), monophosphoryl lipid A, Avridine lipid-amine adjuvant, heat-labile enterotoxin from *E. coli* (recombinant or otherwise), cholera toxin, IMS 1314 or muramyl dipeptide among many others.

Preferably, the adjuvant is added in an amount of about 100 μg to about 10 mg per dose. Even more preferably, the adjuvant is added in an amount of about 100 μg to about 10 mg per dose. Even more preferably, the adjuvant is added in an amount of about 500 μg to about 5 mg per dose. Even more preferably, the adjuvant is added in an amount of about 750 μg to about 2.5 mg per dose. Most preferably, the adjuvant is added in an amount of about 1 mg per dose.

Additionally, the composition can include one or more pharmaceutical-acceptable or veterinary-acceptable carriers. As used herein, "a pharmaceutical-acceptable carrier" or "veterinary-acceptable carrier" includes any and all solvents, dispersion media, coatings, stabilizing agents, diluents, preservatives, antibacterial and antifungal agents, isotonic agents, adsorption delaying agents, and the like.

The compositions and methods of the present disclosure can also comprise the addition of any stabilizing agent, such as for example saccharides, trehalose, mannitol, saccharose and the like, to increase and/or maintain product shelf-life and/or to enhance stability.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, MD 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homologous sequence comprises at least a stretch of 50, even more preferably 100, even more preferably 250, even more preferably 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Those of skill in the art will understand that the composition herein may incorporate known injectable, physiologically acceptable, sterile solutions. For preparing a ready-to-use solution for parenteral injection or infusion, aqueous isotonic solutions, such as e.g. saline or corresponding plasma protein solutions are readily available. In addition, the immunogenic and vaccine compositions of the present disclosure can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others. Suitable adjuvants, are those described above.

In one aspect of the present invention, the immunogenic composition or vaccine includes at least one immunological active component from one or more disease-causing organism in canines or humans in addition to *Rickettsia rickettsii, Ehrlichia chaffeensis, Ehrlichia canis, Ehrlichia ruminantium, Anaplasma marginale, Anaplasma phagocytophilum*, or any combination thereof. Preferably the other disease-causing organism in canine is selected from the group consisting of: rabies, canine parvovirus, canine coronavirus, canine distemper, canine influenza, infectious canine hepatitis, canine herpesvirus, pseudorabies, canine minute virus, brucellosis, leptospirosis, spirochaete, *Borrelia burgdorferi, Rhipicephalus sanguineus, Clostridium perfringens, Clostridium difficile, Bordetella bronchiseptica, Blastomy-* cosis dermatitides, Histoplasma capsulatum, Coccidioides immitis, Coccidioides posadasii, Cryptococcus neofromans, Microsporum canis, Microsporum gypseum, Trichophyton mentagrophytes, Sporothris schenckii, Aspergillus fumigatus, Phythium insidiosum, Mucomycosis, or any combination thereof.

An "immunological active component" as used herein means a component that induces or stimulates the immune response in an animal to which said component is administered. According to a preferred embodiment, said immune response is directed to said component or to a microorganism comprising said component. According to a further preferred embodiment, the immunological active component is an attenuated microorganism, including modified live bacteria, a killed-microorganism or at least an immunological active part of a microorganism.

It must be understood that the present disclosure does not relate to the genomic nucleotide sequences taken in their natural environment, that is to say in the natural state. It concerns sequences which it has been possible to isolate, purify or partially purify, starting from separation methods such as, for example, ion-exchange chromatography, by exclusion based on molecular size, or by affinity, or alternatively fractionation techniques based on solubility in different solvents, or starting from methods of genetic engineering such as amplification, cloning and subcloning, it being possible for the sequences of the disclosure to be carried by vectors.

Complementary nucleotide sequence of a sequence of the disclosure is understood as meaning any DNA whose nucleotides are complementary to those of the sequence of the disclosure, and whose orientation is reversed (antiparallel sequence).

All ranges provided herein include each and every value in the range as well as all sub-ranges there-in-between as if each such value or sub-range was disclosed. Further, all aspects and embodiments of the disclosure comprise, consist essentially of, or consist of any aspect or embodiment, or combination of aspects and embodiments disclosed herein.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

Materials and Methods

Propagation of *R. rickettsii* in Vero cells for preparation of stocks: *R. rickettsii* (Sheila Smith strain) was grown in Vero (African green monkey kidney) cells (clone E6: ATCC CRL-1586) as previously described (Rydkina, E., D. J. Silverman, and S. K. Sahni, (2005), Ammerman, N.C., M. Beier-Sexton, and A. F. Azad, (2008)). Briefly, confluent monolayers of Vero cells grown in DMEM supplemented with 2% fetal bovine serum and 2 mM L-glutamine, were infected with *R. rickettsii* at a multiplicity of infection (MOI) of 0.1 and incubated at 34° C. incubator set at 5% $CO_2$ until ~20% of the monolayer was disrupted due to infection. The rickettsial stocks were prepared by differential centrifugation of lysates from infected cells (Rydkina, E., D. J. Silverman, and S. K. Sahni, (2005)), suspended in K-36 buffer (0.1 M potassium chloride, 0.015 M sodium chloride, 0.05 M potassium phosphate buffer (pH 7.0), and the numbers of viable *R. rickettsii* organisms were determined by plaque titration assay (Rydkina, E., L. C. Turpin, and S. K. Sahni, (2010), Sahni, S. K., D. J. Van Antwerp, M. E. Eremeeva, et al., (1998)).

Propagation of *R. rickettsii* in embryonated chicken eggs: *R. rickettsii* strain Sheila Smith grown in Vero cells was passaged twice in specific pathogen-free (SPF) embryonated eggs (Charles River, CT) as per established protocols (Cox H. R. (1941), Feng H M, Wen J, Walker D H. (1993), Xin L, Shelite T R, Gong B, Mendell N L, Soong L, Fang R, and Walker D H (2012)). The eggs were candled using a transilluminator to mark the air sac, surface sterilized with Providine-iodine, incubated in an egg incubator with carrier rotating ability at 37.5° C. with 65-70% humidity. The development of embryo's vasculature was regularly assessed at 24 h intervals and the eggs with discordant vasculature were discarded. On day 5, a small hole was drilled into the apex of each embryonated egg and 500 µL of diluted *R. rickettsii* stock was injected using a sterile 20 Gauge needle. The hole was sealed with Duco cement glue (VWR, Atlanta, GA) following which infected eggs were incubated at 34° C. for several days and monitored daily for the growth of vasculature and progress of infection. All eggs exhibiting massive vasculature collapse and/or extensive hemorrhage within 72 h of infection were discarded. The vasculature from the remaining eggs was harvested on day 6 or 7 post infection and a small aliquot was plated on blood agar to check for contamination. The harvest from each egg was scored for the level of infection by Diff-Quick staining with 1-4 grades (1=low, 2=moderate, 3=high, and 4=very high) and *R. rickettsii* organisms were purified from the eggs receiving a score of 3 or 4. To ensure complete removal of egg yolk and other proteins as well as cell debris, the harvest was homogenized to release bacteria and passed through a 40 µM cell strainer. The egg harvest containing live rickettsiae was then purified twice by differential centrifugation and the final pellet was suspended in Sucrose-Phosphate-Glutamate (SPG) buffer (0.218 M sucrose, 3.8 mM $KH_2PO_4$, 7.2 mM $K_2HPO_4$, 4.9 mM monosodium 1-glutamic acid, pH 7.0) aliquoted, and stored at −80° C. until use. The viability and infectivity of the stock was quantified by plaque formation assay on Vero cell monolayers (Rydkina, E., L. C. Turpin, and S. K. Sahni, (2010), Sahni, S. K., D. J. Van Antwerp, M. E. Eremeeva, et al., (1998)).

ADR2 and OmpB-4 recombinant plasmid constructs and protein expression and purification: The pET28a vector (Novagen, Madison, WI) encoding *R. rickettsii* gene Adr2 and gene fragment of OmpB-4 were prepared to overproduce recombinant proteins Adr2 and OmpB-4 for purification, respectively (Gong W et al 2015). The entire protein coding sequence of Adr2 and similarly the coding sequence of OmpB-4 were amplified by PCR from *R. rickettsii* genomic DNA using Q5 High-Fidelity DNA polymerase (New England Biolabs) with the gene-specific PCR primers that encompassed flanking NdeI at the beginning of the forward primer end and XhoI also at the 5' end of the revere primer (Supplement Table 1), respectively. The PCR products were subsequently cloned into pET28a plasmid at the above restriction sites after digesting both plasmid and inserts and ligating using T4 DNA ligase. The resultant recombinant constructs contain an N-terminal His6-tags. Recombinant Adr2 and OmpB-4 were overexpressed in *E.* coli BL21 (DE3) following the plasmids' transformation. Subsequently, the recombinant proteins expressions in the E. coli strain were induced by adding 1 mM isopropyl-β-D-thiogalactopyranoside (IPTG) at 1 mM by growing at 30° C., and the proteins were then purified using Ni-NTA-agarose (Qiagen, Germany) as per the manufacturer's protocols (Novagen). The final concentration of purified recombinant proteins was estimated by the Bradford method using a Bio Rad protein assay kit (Bio Rad, Hercules, CA).

Vaccine formulations: Complete Freund's Adjuvant and Incomplete Freund's adjuvant (Sigma-Aldrich, St. Louis, MO) or Montanide™ gel (SEPPIC INC., Fairfield, NJ) at a concentration of 2.5% prepared in PBS were used as adjuvants. Whole cell antigen vaccines (WCA) are prepared by mixing with 70 µg of inactivated R. rickettsii whole cell derived antigens to a final concentration of 1 ml in PBS containing the respective adjuvant. Whole cell inactivation was prepared by incubating the cultured organisms in PBS.

Experimental infections in dogs: Experiments with dogs complied with the Public Health Service (PHS) Policy on the Humane Care and Use of Laboratory Animals, the US Department of Agriculture's (USDA) Animal Welfare Act & Regulations (9CFR Chapter 1, 2.31), and were performed with approval of the Kansas State University (KSU) Institutional Animal Care and Use Committees (IACUC) as per the guidelines of the protocol. Purebred beagle dogs (4-6 month old of both sexes) were purchased from a Class A USDA vendor (Covance Research Products, Denver, PA) and housed in indoor climate controlled facilities at Kansas State University as previously described (Nair A D. et al 2016). Dogs were provided a commercially available dry dog food and water ad libitum and were also provided adequate space allowing them to freely move about for regular exercise activity. All groups of dogs independent of vaccinated or not, or infected or non-infected controls were monitored daily for health and behavioral changes and twice weekly for body temperature and hematological changes.

Dogs were infected with *R. rickettsii* Sheila Smith strain ($10^5$) in 0.5 ml PBS/dog via I.V. inoculation. Dogs were monitored daily for fever, and clinical signs of the disease. Rectal temperatures were monitored daily, while body weights were measured once a week. Blood samples were collected in EDTA tubes from the cephalic vein, every 2 days, from 0 through 11 days post-inoculation (dpi). At the end of each experiment, all animals were euthanized in accordance with the recommendations of the Panel on Euthanasia of the American Veterinary Medical Association (AVMA). A commercial euthanasia solution, Fatal-Plus1, of volume 0.22 ml/kg containing 86 mg/kg of pentobarbital was administered intravenously. All dogs received diphenhydramine syrup (4 mg/kg body weight) about 30 min before infection challenge to avoid any possible anaphylactic shocks.

Three infection experiments; one to define the RMSF disease and two in support of vaccine studies were conducted to evaluate the vaccine potential of RMSF WCA antigens. The first vaccine study included the use of Complete Freund's Adjuvant (CFA) as part of the primary vaccination followed by the use of Incomplete Freund's Adjuvant (ICFA) for the booster vaccination as the adjuvants, while the second vaccination experiment included Montanide pet gel as the adjuvant. The first vaccine study included four groups of dogs (n=3) where groups 1 and 2 received WCA and recombinant antigen (RCA) (70 μg each) as the vaccines, respectively, while group 3 received only adjuvant mixed with phosphate buffer saline and group 4 received only phosphate buffer saline. After two vaccinations separated by four weeks apart, groups 1, 2 and 3 received infection challenge by I.V. inoculation with 1 ml of *R. rickettsii* culture suspensions containing $10^5$ bacteria on day 56, while group 4 did not receive infections to serve as uninfected controls. All 12 dogs were monitored daily for the clinical signs of RMSF disease.

The second infection experiment was carried out in three dogs receiving chicken egg passaged $10^5$ *R. rickettsii* organisms, while the second vaccination experiment was similar to the first vaccination experiment, except that n=6 for each group. After the infection challenge, clinical signs and food consumption were monitored, and rectal temperatures were recorded. Blood from the cephalic vein was collected in EDTA tubes every 2 days from day 0 until end of experiment. Blood samples were assessed once a week for hematological changes by performing the complete blood counts at the Kansas State Veterinary Diagnostic Laboratory. Similarly, serological analysis was performed for measuring the IgG response against bacterial antigens and likewise, nested PCR analysis was performed to detect the presence of bacteria DNA. Body temperatures were monitored twice a week following vaccinations and daily following infection challenges.

Rickettsial DNA assessed by nested PCR and IgG response assessed by ELISA: Whole blood samples from dogs were collected aseptically into either 12 ml vacutainer tubes (Corning Inc., Lowell, MA) containing EDTA (Sigma Aldrich, St. Louis, MO) or Microtainer serum separator tubes (Becton Dickinson and Co., Franklin Lakes, NJ) for the detection of *Rickettsia* by PCR and serum for the detection of anti-*R. rickettsii* antibodies, respectively. Genomic DNA was isolated from blood samples using DNeasy Blood and Tissue kit (Qiagen, Valencia, CA, U.S.A.), according to the manufacturers protocol. DNA samples were stored at −20° C. until tested by PCR for the presence of *R. rickettsii* DNA and sera samples were similarly stored at −20° C. until serologic testing was performed. The presence of Rickettsial DNA was detected by PCR and nested PCR methods using Adr2-NF2 and Adr2-NR2 primers to amplify fragments of the Adr2 gene of *Rickettsia* spp. All DNA samples were tested in duplicate. A no template reaction was included to serve as a negative control and similarly, a positive control reaction included *R. ricketsii* genomic DNA as the template as part of each PCR set up. The PCRs were performed in a GenAmp 9700 instrument (Applied Biosystems, Foster City, CA). Briefly, the first round of PCR was carried out in a 25 μl reaction volume using Platinum Taq DNA polymerase (Life Technologies, Carlsbad, CA, USA) and the nested PCRs were performed using 2 μl of 1:100 diluted products from the first PCR. Annealing temperature was 55° C. and extension times were 30 sec and 60 sec. for 40 cycles. Products from the second PCR were resolved on a 1.5% agarose gel to identify specific sized amplicons by following standard molecular methods (Sambrook J, Russell D W, 2000). Positive product specificity was further confirmed by sequencing of several randomly selected samples.

ELISA for *R. rickettsii* specific IgG: The ELISAs were performed using *R. rickettsii* inactivated whole cell antigens or using recombinant protein antigens. Serum samples from all dogs collected prior to infection and several days following, vaccinations and infection challenges were assessed by ELISA for the presence of the *R. rickettsii*-specific IgG as previously described (Nair A D et al 2014). Briefly, the 96-well Immulon 2HB ELISA plates (Thermo Fisher Scientific, Waltham, MA) were coated with the inactivated whole cell antigen, or with the recombinant Adr2 and OmpB-4 at a concentration of 20 ng/well prepared in 50 mM sodium carbonate buffer, pH 9.6. Serum sample were diluted 1:50 in PBS, added to triplicate antigen-coated wells and incubated for 2 h at room temperature. The wells were then washed thrice with PBS containing 0.05% Tween 20 (PBST) and incubated with HRP-conjugated goat anti-dog total IgG (Bethyl Laboratories, Montgomery, TX) at a dilution of 1:40,000. Unbound secondary antibodies were removed by washing with PBST three times, and the specific interactions were assessed by color development using TMB (3, 30, 5, 50-tetramethyl benzidine) (Calbiochem, San Diego, CA) as the substrate.

ELISA for Canine IFNγ: Peripheral blood mononuclear cells (PBMC) were collected on the indicated days after RMSF challenge. Cells were isolated by density centrifugation from buffy coat fractions of peripheral blood collected into 2× acid citrate dextrose. Cells were washed and resuspended in complete RPMI composed of RPMI-1640 (Gibco, Carlsbad, CA) supplemented with 2 mM L-glutamine, 25 mM HEPES buffer, 1% antibiotic-antimycotic solution, 50 mg/mL gentamicin sulfate, 1% nonessential amino acids, 2% essential amino acids, 1% sodium pyruvate, 50 μM 2-mercaptoethanol, and 10% (v/v) fetal bovine serum. Cells were cultured at 37° C. with $4 \times 10^5$ cells/well in 96-well plates and were stimulated with 10 μg/mL whole cell antigen. As a positive control, cells were stimulated with 5 μg/mL Concanavalin A (Sigma-Aldrich). Negative control wells remained unstimulated. PBMC culture supernatants were collected after 5 days of stimulation and canine IFNγ protein concentrations were determined by commercial ELISA kit (R&D Systems, Minneapolis, MN) per manufacturer's instructions.

Histopathology analysis: Selected tissues, including cerebrum, cerebellum, brain stem, lung, liver, testicle and epididymis, were fixed in 10% neutral buffered formalin and processed routinely with hematoxylin and eosin at 4 μm sections prepared by the KSVDL histology laboratory service. All slides were then reviewed by two pathologists (co-authors; AC and JH) where they did not know sample assignments during the analysis (a blind study). A, comprehensive numeric score was developed to grade the severity and distribution of inflammation in all organs examined. Inflammation within a tissue was divided into perivascular inflammation (PVI) and non-perivascular inflammation (NPVI) both of which were assigned scored ranging from 0 to 3. The degree of severity of PVI was classified as follow: 0 refers to no perivascular inflammation; 1 represents the presence of one cell thick perivascular cuffing; 2 refers to 2-3 cell thick perivascular cuffing; and 3 signifies to more than 3 cells thick, perivascular cuffing. Additionally, the distribution of inflammation was classified as 0 for no inflammation; 1 refers to single foci of inflammation; 2 to designate 2-4 foci of inflammatory infiltrate and 3 is to represent greater than 5 inflammatory foci within a tissue examined (supplementary Table S1). The overall predominant cell types were also assessed in each inflammatory foci for all organs assessed to distinguish perivascular from non-perivascular inflammations. Zonal distribution was noted in liver sections spanning periportal regions (PP), central veins (CV) and in other randomly found regions (R). Similarly, we assessed for the presence of intratubular, multinuclear giant cells within the testicle and epididymis. After completing the analysis, mean values were calculated for all tissues of each animal and the animals' identities were assigned to the respective experimental groups. Subsequently, organ-based inflammatory assessment scores were generated based on the average values for each animal group and statistical analysis was performed using the ANOVA software program. Treatment group to control comparisons were considered significant ($p<0.05$) or different if the Bonferroni p value was less than 0.05.

Results

Assessment of recombinant and whole cell inactivated vaccines to confer protection against infection challenge with *R. rickettsii*: We initiated studies to investigate if two immunodominant recombinant antigens (Adr2 and OmpB-4) as a subunit vaccine (RCA) and/or whole cell-derived inactivated antigens of *R. rickettsii* as a vaccine (WCA) in conferring protection against infection challenge with in vitro continuously grown, Vero cell culture-derived *R. rickettsii*. ADR2 and OmpB-4 were chosen for the subunit vaccination formulation as prior reports in the murine host suggested that they are immunogenic and may offer protection (Gong W et al 2014, Gong W et al 2015). Whole cell inactivated antigens were similarly selected because; prior studies with formalin fixed *R. rickettsii* organisms appear to offer protection against infection challenge (Gonder et al 1979, Tones J F, et al 1995, Geeraedts F, et al 2008). Recombinant Adr2 and OmpB-4 were prepared using an *E. coli* expression system, while the WCA were prepared from the continuously cultured *R. rickettsii* in Vero cells. In this first vaccine experiment, we used the Complete Freund's Adjuvant (CFA) to serve as the adjuvant in the vaccine formulations to stimulate immunity, followed by the use of Incomplete Freund's adjuvant (ICFA) in the booster vaccination. In particular, we opted these adjuvants as prior canine vaccine studies suggest that they offer strong host responses (Poota J et. al 2009). Further, continuously cultivated *R. rickettsii* at a dose of 105 organisms were used for infection challenge in the canine host studies (refs). The WCA and RCA concentrations were kept at 70 μg per inoculum in the vaccine preparations in 1 ml volume. Four groups of dogs (n=3) were used where one group each received WCA and RCA as the vaccines, respectively, while three animals received only the diluted adjuvant and the fourth group of animals was kept as non-infection controls, which received only PBS. Animals in the first two groups received second vaccination after 35 days and similarly, the third group animals received adjuvant booster. Thirty three days following the booster vaccination/adjuvant treatments, dogs in groups receiving RCA, WCA or adjuvant only, were challenged with the I.V. infection inoculum, while the last group dog were kept as the uninfected controls. All 12 dogs were monitored daily for the clinical signs, apatite, and behavioral changes, such as socialization with other dogs within each group and with people engaged in the project. Dogs were also monitored weekly by CBC analysis to assess changes in the blood profiles.

All dogs in first three groups which received the CFA as the adjuvant, independent of infection challenge, developed severe inflammation at the inoculation sites, which progressed to persisting major puss producing blisters. Those dogs required the detailed clinical care involving pharmacological interventions to reduce both inflammation and non-specific wound infections. The adjuvant-associated clinical illness also required us to delay the booster vaccination and infection challenge experiments by about one week each, respectively. Clinical sings in dogs receiving infection inoculum were also milder. One dog each from RCA vaccinated and non-vaccinated infection group exhibited partial paralysis and mild fever and were sacrificed on 11 days post infection. The remaining animals from the two groups appeared normal following infection challenge, although mild fever persisted at times. Non-infected control group and WCA vaccinated group dogs appeared healthy, with no obvious clinical signs. Hematological assessment did not suggest any notable changes, with the exception of occasional rise in the neutrophil numbers and drop in hemoglobin and PCVs (not shown). Nested PCR analysis to determine the presence of rickettsial DNA in blood revealed minor differences in RCA or WCA vaccinated dogs compared to infection control group animals. All non-infected control animals were negative for the DNA by PCR analysis, while WCA, RCA and non-vaccinated animals had occasional PCR positives with significant differences noted among the three groups (not shown).

All dogs receiving WCA or RCA vaccines had detectable IgG responses against the respective antigens, and the responses increased following booster vaccinations. Non-vaccinated group dogs had no $R.$ $rickettsii$ antigen-specific IgG responses. The bacterial antigen-specific CD4+ T-cell proliferation in vitro in PBMCs and IFN-γ production was observed only for the WCA vaccinated dogs. The induction of antigen-specific IgG response and the in vitro T-cell proliferative responses with IFN-γ production following vaccination with WCA, coupled with the apparent absence of clinical signs in this group suggest that this vaccine has a better protective host response. However, dogs in RCA vaccinated and non-vaccinated infection controls also had milder clinical signs. We reasoned that the continuously cultured Vero cell-derived $R.$ $rickettsii$ inoculum is not sufficiently virulent to cause the severe RMSF disease. Consistent with these observations, pathological assessment of various tissue samples revealed only occasional macro and micro lesions in infected dog tissues, independent of the animals receiving vaccinations (not shown). Although the lesions were consistent with the RMSF pathology in the infection dogs, there was little correlation observed for vaccinated vs non-vaccinated dogs. We reasoned that vaccine assessment studies require improvements to the following; 1) develop a virulent infection model with clear RMSF disease outcome and 2) replace CFA with a safer adjuvant that is sufficiently immunogenic, but does not induce adjuvant-associated inflammatory disease.

Clinical disease in dogs with egg passaged *R. rickettsii: R. rickettsii* is known to lose virulence if continuously cultured in vitro and that the virulence may be restored if the organisms are recovered from an infected chicken embryo (Cox, H. R. 1938). To develop a virulent infection model in dogs having a severe RMSF disease, we grew *R. rickettsii* by infecting chicken egg embryos and subsequently, the organisms were recovered for use as an inoculum for the infection assessment. Three 6 month-old dogs (males) received I.V. inoculation with chicken egg embryo-derived *R. rickettsii* and were followed for the development of RMSF disease; indeed, all the three dogs developed sever clinical manifestations starting from day 3-post infection. The dogs had persistent fever (≥103° C.) until the last day of infection assessment (7-10 days post infection). All three dogs also were severely depressed, as judged by their lack of interest to socialize and decreased appetite. Further, they exhibited petechial rashes on ears, gums, buccal mucosa and testis. The rashes and inflammation were more prominent on testis as evidenced by the increased swelling and darkened scrotal skin by day 5 post infection. The dogs also developed edema at various places, including on the face and feet. In addition to edema and severe depression, the dogs were also severely dehydrated and lost desire to eat or drink. All three dogs were etherized; one on day 7 and two on day 10 because of the increased severity of clinical signs. The CBC analysis, performed daily on all three animals, revealed a significant drop in hemoglobin, RBC numbers, and packed cell volume, while elevated levels of monocytes and neutrophils were observed on the day of sacrifice. All three dogs also had persistent bacteremia, which was observed from day two onwards, as judged by the nested PCR analysis. Pathological assessment of various tissue samples revealed macro and micro lesions that are consistent with RMSF disease in dogs. Together, these data suggest that the egg embryo-passaged *R. rickettsii* at the dose of $10^5$ organisms are sufficient to provide characteristic signs of the RMSF disease.

Assessment of recombinant and whole cell inactivated vaccines to confer protection against challenge with virulent *R. rickettsii*: We reevaluated the WCA and RCA vaccines for protection against virulent infection challenge with egg-passaged *R. rickettsii* as the infection inocula. In this experiment, we used the Montanide pet gel in place of CFA as an adjuvant. Prior studies suggest that Montanide pet gel stimulates a strong host response with vaccine antigens, while not initiating adjuvant-associated disease in dogs (Jang S I et al 2011, Cauchard S et al. 2014, Liu X et al 2014). We used 2.5% of Montanide pet gel, in place of the prior established 5% concentration, to avoid any possibility of developing inflammation (as per personal communications and recommendations of the adjuvant vendor; SEPPIC, France). Four groups of dogs were used (n=6; 3 males and 3 females in each group) where one group each received adjuvant mixed WCA or RCA or adjuvant alone, while the last group (n=3) was kept a non-vaccinated and non-infected. The adjuvant-vaccine formulations or adjuvant alone injections were repeated after four weeks and the first three groups of dogs were challenged with $10^5$ organisms of egg passaged virulent *R. rickettsii*. Dogs from all groups were monitored for the development of inflammation at the injection sites, and clinical and behavioral signs were monitored daily for the after primary and booster vaccinations and following the infection challenge. Body temperatures were also monitored daily following infection challenge. The CBC analysis and weights were assessed every week throughout the study period.

Montanide™ Gel did not induce inflammation at the inoculation sites and neither altered the blood profiles. Following infection challenge, four dogs in the WCA vaccinated group had a mild fever on day 2 post infection, while all dogs in RCA vaccinated and non-vaccinated infection group developed fever on several days post infection beginning from day 2. Further, RMSF-characteristic petechial rashes were observed on ears, gums, and testis (for males) for all animals in infection control group as well as in the RCA vaccinated group, while only one dog from WCA vaccinated group on day 6 after infection had mild rashes on the ears. Additional clinical signs included swelling on ears, feet, snout, testes and on the face of several dogs from the RCA vaccinated and infection control groups. Further several dogs from RCA and infection control groups became lethargic, too weak to walk or socialize and had a loss of appetite within few days following infection challenge; five dogs from infection control group and four dogs from RCA vaccinated group required euthanasia by day 7 post infection challenge. Although fever and rashes were observed, one dog each in RCA and infection control group improved after few days and so these they were maintained with supporting care till the study end. Pathological assessment of tissue samples collected from cerebrum, cerebellum, brainstem, lung and liver revealed lesions consistent with RMSF etiology only in the RCA and infection control groups, while dogs vaccinated with WCA and non-infected controls looked similar with no notable lesions. Non-infected and WCA vaccinated dogs had the lowest inflammatory scores in all tissues samples assessed. Although lung and liver tissues had some inflammatory scores in these two groups, the scores were significantly less compared to those observed for dogs in RCA vaccinated and receiving only *R. rickettsii* infection. The highest inflammatory scores were observed in all tissues examined for these two groups compared to the WCA vaccinated and uninfected controls (p values=>0.05). The most affected organs in all groups were lungs and livers. Although the inflammation was notable in WCA and non-infected dogs for the two tissues, it was significantly more for dogs within the infection controls or RCA vaccinated. Importantly, inflammatory scores are very similar for dogs in the infection controls and RCA vaccinated. Similarly, there was no significant difference among the dogs receiving WCA vaccine and non-infection controls.

Genomic DNAs recovered from blood samples collected over time and from spleen, liver and lung and brain tissues recovered at the terminal time point from all four groups of dogs were assessed by nested PCR. Following infection challenge, all dogs receiving only infection tested positive for the *R. rickettsii* DNA starting from day 4 and remained frequently positive till the terminal day of the study. Similarly, four RCA vaccinated dogs tested positive frequently, while two dogs from WCA vaccinated group tested positive on day 4 and one dog on day 6 and another dog on day 17. Lung, liver, spleen and brain tissues also tested positive for the *R. rickettsii* genomic DNA for 5 out of 6 dogs in the infection control group, while three RCA vaccinated group dogs tested positive for DNA in lung, liver or spleen tissues. Tissue samples for all dogs from the WCA vaccinated and uninfected controls were negative for the bacterial DNA. Dogs from RCA vaccinated and infection control groups had an average weight loss of about 7-8%, while dogs in the WCA vaccinated and uninfected control groups had weight gain of 8% (not shown). Hematological assessment revealed the drop in hemoglobin, RBC numbers and packed cell volumes on day 7 post infection challenge only for dogs receiving RCA vaccine and infection controls, while WCA vaccinated and non-infected control groups had normal hematological values (not shown). Elevated levels of leucocytes were detected in all three groups of dogs receiving infection.

*R. rickettsii* whole cell antigen-specific IgG responses were observed for WCA vaccinated group after both primary and booster vaccinations; the IgG levels increased after booster vaccination and remained high after infection challenge. While RCA vaccination also induced *R. rickettsii*-specific IgG, the response was considerably less compared to WCA vaccinated dogs. The IgG levels were detectible for this group only after booster vaccination and following infection challenge. Dogs in the infection control group also induced IgG response, but only following the infection challenge, while non-infected dogs were negative for the antibody throughout the study. The T-cell proliferations were observed for animals vaccinated with WCA or RCA (not shown), while IFNγ producing T-cells were detected only from WCA vaccinated group dogs on day 7-post infection challenge. Dogs receiving infection following vaccination with WCA were healthy and appeared similar to the uninfected controls, while those from RCA vaccinated group were similar to infection controls in developing a severe RMSF disease.

Discussion

RMSF has been known for over a century as the most lethal tick-borne disease and is also considered as the most lethal infectious diseases known in the Americas due to the high case fatality rates reported with *R. rickettsii* infections. For example, RMSF fatality rates in Mexico documented over a century range from 30-80% (Straily A et al. 2016, Gerardo Álvarez-Hernández et al. 2017). The disease fatalities remained high (>40%) also in recent years according to the recent epidemiological data and similarly the fatal RMSF cases are frequently documented in companion animals, dogs (Horta M C et al 2004, Kidd L et al 2006, Hii S F et al 2011, Labruna M B et al. 2009). Despite the enormous importance, measures to contain RMSF in either dogs or people are virtually non-existant. Likewise, therapeutic options against the RMSF are limited only to tetracycline derivatives, such as doxycycline. While prior investigations dating back several decades suggest the protective host response with formalin fixed *R. rickettsii* and similarly recent studies identified few immunogenic antigens as likely candidates for vaccine development, the RMSF vaccine research is largely unexplored.

One of the major limitations of the research on RMSF is the lack of infection models having clinically relevant disease outcomes to study vaccine efficacies. Much of the animal studies are carried out using the murine host or with the Guinea pig infection model, with few descriptions of infection studies in dogs (Sumner J W et al 1995, Eliane M Piranda et al. 2008, Wang P et al. 2017). The rodent hosts are naturally not known to acquire *R. rickettsii* infections or in developing RMSF clinical disease. A second possible challenge to investigate the development of RMSF vaccines has been the high containment facility requirements for culturing *R. rickettsii* and performing certain procedures when working with infected animals. In the current study, we focused our efforts in reproducing the infection model using a physiologically relevant host, dog, and subsequently two vaccine formulations were assessed for their value in protecting against the severe RMSF disease. In our initial experiments, continuously cultivated Vero cell culture-derived *R. rickettsii* organisms as the infection inoculum was used to reproduce RMSF in dogs. We also investigated the use of two types of vaccines; a vaccine constituting of two outer membrane protein antigens, Adr2 and OmpB-4 (RCA) or the whole organism-derived antigens (WCA) combined with the Freund's complete adjuvant for the first vaccination in the canine model. The Freund's complete adjuvant was opted, as it is well known to induce a strong immune response, including in the canine host (Terkawi M A et al 2007, Haghighat S et al. 2017). However, this adjuvant triggered a severe inflammatory disease in dogs independent of the inclusion of vaccine antigens. The adjuvant-induced disease required supporting care and pharmacological interventions to treat the wounds at vaccination sites. The adjuvant-associated inflammation was not well described in the literature for dogs, although the *Mycobacterium tuberculosis* antigens, present in this adjuvant, are long known to boost a strong immune response with vaccine antigens and also in inducing vaccine-independent inflammatory disease in various vertebrate host species (von Reyn C F et al 1998). From our current study, we realized that this adjuvant is not well suited for canine vaccine studies. As the adjuvant induced a severe inflammatory disease, independent of the inclusion of vaccine antigens, we believe that caution must be exercised when considering this adjuvant in the formulations of any kinds of canine vaccines.

Despite prior studies documenting that the $10^5$ *R. rickettsii* organisms are sufficient in inducing a virulent disease in dogs (refs), our study suggested that this dose did not stimulate a classical RMSF disease in dogs when the inoculum was prepared from the continuously cultivated Vero cell derived bacteria. We reasoned that the failed reproduction of the clinical disease in the canine host might have resulted due to pathogen's loss of virulence in continuous in vitro propagation. To restore the virulence, *R. rickettsii* organisms were first propagated in chicken eggs and then passaged once in Vero cells (Cox, H. R. 1938). Indeed, the I.V. inoculation of $10^5$ *R. rickettsii* organisms derived from infected chicken egg embryos are sufficient in causing the classical RMSF disease within a few days after infection challenge in dogs. Clinical signs included persistent high fever, petechial rashes, rapid discoloration of scrotum, edema on the face and legs, rapid weight loss and apatite and the development of severe depression in all infected dogs. Further, pathological analysis of tissue samples collected from terminally sacrificed animals revealed infection-associated lesions only in dogs receiving the infection. The clinical and histopathology data were also consistent with the RMSF clinical disease in the canine host.

The development of RMSF disease model in dogs was the critical first step in evaluating the efficacy of vaccines. While both RCA and WCA vaccines prepared using Montanide™ gel as the adjuvant induced *R. rickettsii*-specific IgG responses, only WCA conferred complete protection against the clinical disease. The Montanide™ gel did not promote an inflammatory response, like that observed in the Freund's complete adjuvant. Despite high similarity in the RCA and WCA vaccinated group in stimulating the *R. rickettsii* antigen-specific IgG responses, only the WCA vaccinated group had detectable IFNγ secretions at day 7 post infection challenge in the PBMCs stimulated with the whole cell *R. rickettsii* antigens. While much remains to be determined regarding the molecular basis for inducting protection against the RMSF disease by WCA, the evidence from the current study suggests that recombinant ADR2 and OmpB-4 are not sufficient in promoting complete protection against the disease, as predicted from the murine host experiments (refs). Our study suggests that T- and B-cell responses spanning to a broader range of the bacterial antigens is necessary in developing a protective host response. This study also provides the first evidence that WCA-based vaccine when administered as two subcutaneous injections spreading apart by four weeks is sufficient in conferring protection against the fatal RMSF disease. The WCA vaccine also appeared to offer sterile immunity, as evidenced by the molecular analysis. Genomic DNA recovered from blood sampled at various time points post infection challenge and similarly in various tissue samples collected after four weeks following the infection challenge tested negative in all dogs in the WCA vaccinated group, except for one time point in one dog. The presence of amplifiable DNA in only one blood sample from one dog may likely represent a false positive occurrence of the assay. Alternatively, the bacterial numbers may have dropped far below to the detection levels of the molecular assay sensitivity resulting from the immune induction by WCA vaccination. While the results from the current study offer the first evidence of vaccine-induced protection with WCA, it is yet to be determined if the RMSF clinical disease resulting from the tick transmission may similarly be eliminated by the WCA. Further, the additional investigations are needed in defining the minimum vaccine dose required, immunological basis for the vaccine-induced protection, and the extent of protection conferred with the WCA.

In summary, this study is the first in evaluating the efficacy of two types of vaccines against RMSF disease; a subunit vaccine containing two immunogenic outer membrane protein antigens or whole organism-derived antigen vaccine. We developed a more relevant animal model for RMSF disease, as dogs are naturally known to develop RMSF. In an effort to identify the best vaccine in inducing the protective immunity, two adjuvants known to offer best immune induction; Freund's complete adjuvant and Montanide pet gel, were also investigated. While both adjuvants and both vaccine formulations induce good immune induction, adjuvant-associated clinical disease was observed only with the Freund's complete adjuvant, while Montanide per gel appeared completely safe. The data presented in this study demonstrate that only the WCA gives the complete protection against the classical canine RMSF disease.

Example 2

Materials and Methods

This example will test a whole cell vaccine comprising inactivated *Ehrlichia chaffeensis, Ehrlichia canis, Ehrlichia ruminantium, Anaplasma marginale,* or *Anaplasma phagocytophilum*, and any combination thereof. The protocol for producing the whole cell vaccine and for testing vaccine efficacy will be performed as in Example 1.

Results and Conclusions

The results will show that the immunogenic composition or vaccine will provide a protective immune response in the dogs, lessening the incidence of infection and incidence as well as severity of clinical symptoms and signs associated with infection of *Ehrlichia chaffeensis, Ehrlichia canis, Ehrlichia ruminantium, Anaplasma marginale,* or *Anaplasma phagocytophilum*.

What is claimed is:

1. An immunogenic composition comprising:
   a first inactivated whole cell bacteria selected from the group consisting of *Rickettsia rickettsii, Ehrlichia chaffeensis, Anaplasma marginale, Anaplasma phagocytophilum*, and any combination thereof; and
   an adjuvant, selected from the group consisting of Quil A, aluminum hydroxide, montanide, and any combination thereof.

2. The composition of claim 1, further comprising an additional component selected from the group consisting of veterinary-acceptable carriers, solvents, dispersion media, coatings, stabilizing agents, diluents, preservatives, antibacterial and antifungal agents, isotonic agents, adsorption delaying agents, compositions known to increase immunity, and any combination thereof.

3. The composition of claim 1, wherein the composition includes at least one second inactivated whole cell bacteria selected from the group consisting of *Rickettsia rickettsii, Ehrlichia chaffeensis, Anaplasma marginale*, and *Anaplasma phagocytophilum*, and any combination thereof.

4. The composition of claim 1, further comprising at least one antigen from a disease-causing organism in canine selected from the group consisting of: rabies, canine parvovirus, canine coronavirus, canine distemper, canine influenza, infectious canine hepatitis, canine herpesvirus, pseudorabies, canine minute virus, brucellosis, leptospirosis, spirochaete, *Borrelia burgdorferi, Rhipicephalus sanguineus, Clostridium perfringens, Clostridium difficile, Bordetella bronchiseptica, Blastomycosis dermatitidis, Histoplasma capsulatum, Coccidioides immitis, Coccidioides posadasii, Cryptococcus neofromans, Microsporum canis, Microsporum gypseum, Trichophyton mentagrophytes, Sporothris schenckii, Aspergillus fumigatus, Phythium insidiosum*, Mucomycosis, or any combination thereof.

5. The composition of claim 1, wherein the inactivated whole cell bacteria is *Rickettsia rickettsii*.

\* \* \* \* \*